(12) United States Patent
Damotharan et al.

(10) Patent No.: US 9,782,468 B2
(45) Date of Patent: Oct. 10, 2017

(54) PURIFICATION OF POLYSACCHARIDE PROTEIN CONJUGATES

(71) Applicant: Shantha Biotechnics Private Limited, Hyderabad, Telangana (IN)

(72) Inventors: Vijayarangam Damotharan, Telangana (IN); Sandeep Kumar Nettem, Telangana (IN); Raghavendra Maila, Telangana (IN)

(73) Assignee: Shantha Biotechnics Private Limited, Hyderabad, Telangana (IN)

(*) Notice: Subject to any disclaimer, the term of this patent is extended or adjusted under 35 U.S.C. 154(b) by 0 days.

(21) Appl. No.: 14/785,247

(22) PCT Filed: May 15, 2014

(86) PCT No.: PCT/IB2014/061456
§ 371 (c)(1),
(2) Date: Oct. 16, 2015

(87) PCT Pub. No.: WO2014/188313
PCT Pub. Date: Nov. 27, 2014

(65) Prior Publication Data
US 2016/0067325 A1    Mar. 10, 2016

(30) Foreign Application Priority Data

May 20, 2013  (IN) .......................... 2201/CHE/2013

(51) Int. Cl.
| | |
|---|---|
| *C12N 9/52* | (2006.01) |
| *A61K 47/48* | (2006.01) |
| *C12N 9/96* | (2006.01) |
| *A61K 39/102* | (2006.01) |
| *C07K 1/16* | (2006.01) |
| *C07K 1/34* | (2006.01) |
| *C07K 1/36* | (2006.01) |
| *A61K 39/00* | (2006.01) |

(52) U.S. Cl.
CPC ...... *A61K 39/102* (2013.01); *A61K 47/48261* (2013.01); *C07K 1/165* (2013.01); *C12N 9/52* (2013.01); *C12N 9/96* (2013.01); *A61K 2039/6037* (2013.01); *C07K 1/34* (2013.01); *C07K 1/36* (2013.01); *C12Y 304/24068* (2013.01)

(58) Field of Classification Search
CPC .......... A61K 2039/6037; A61K 39/102; A61K 47/48261; C07K 1/165; C07K 1/34; C07K 1/36; C07K 14/34; C07K 14/505; C07K 1/16; C07K 1/18; C07K 1/20; C07K 1/22; C12N 9/52; C12N 9/96
See application file for complete search history.

(56) References Cited

U.S. PATENT DOCUMENTS

| | | |
|---|---|---|
| 6,284,250 B1 | 9/2001 | Lees et al. |
| 6,572,766 B1 | 6/2003 | Bergstrom et al. |
| 7,208,093 B2 | 4/2007 | Berg et al. |
| 8,383,783 B2 | 2/2013 | Lees et al. |

FOREIGN PATENT DOCUMENTS

| | | | |
|---|---|---|---|
| EP | 0 665 020 A2 | * | 8/1995 |
| WO | WO2008073620 A2 | | 6/2008 |
| WO | WO2009014481 A1 | | 1/2009 |
| WO | WO2009099375 A1 | | 8/2009 |
| WO | WO2009131526 A1 | | 10/2009 |
| WO | WO2010005364 A1 | | 1/2010 |

OTHER PUBLICATIONS

Applicatio Note: Purification of influenza A/H1N1 using Capto Core 700, GE Healthcare, 29-0003-34, Edition AB (2012).
Zhao et al., Ligands for mixed-mode protein chromatography: Principles, characteristics and design, J Biotechnol. Oct. 12, 2009;144(1):3-11.
Lundgren, Enhanced processing of egg-based vaccines, GE Healthcare Bio-Sciences AB, 2011, 29 pages.
Jagschies, Novel technology creating agility in vaccine manufacturing, Terrapin World Vaccine Congress, Washington DC, Apr. 2011, 25 pages.
Capto Core 700, GE Healthcare Life Sciences, Data file 28-9983-07 AA, Multimodal chromatography, Mar. 2012, 4 pages.
Capto Core 700, GE Healthcare Life Sciences, Instructions 28-9958-80 AC, Core beads, Mar. 2012, 24 pages.

* cited by examiner

*Primary Examiner* — Padma V Baskar
(74) *Attorney, Agent, or Firm* — Rudy J. Ng; Bret E. Field; Bozicevic, Field & Francis LLP

(57) ABSTRACT

The invention describes a method of purifying polysaccharide protein conjugates using mixed mode chromatography. The method involves contacting a crude polysaccharide protein conjugate with a mixed mode resin comprising an inert porous shell and an activated core under conditions of low conductivity that allow binding of the contaminants and collecting the unbound polysaccharide protein conjugate in a flowthrough.

25 Claims, 3 Drawing Sheets

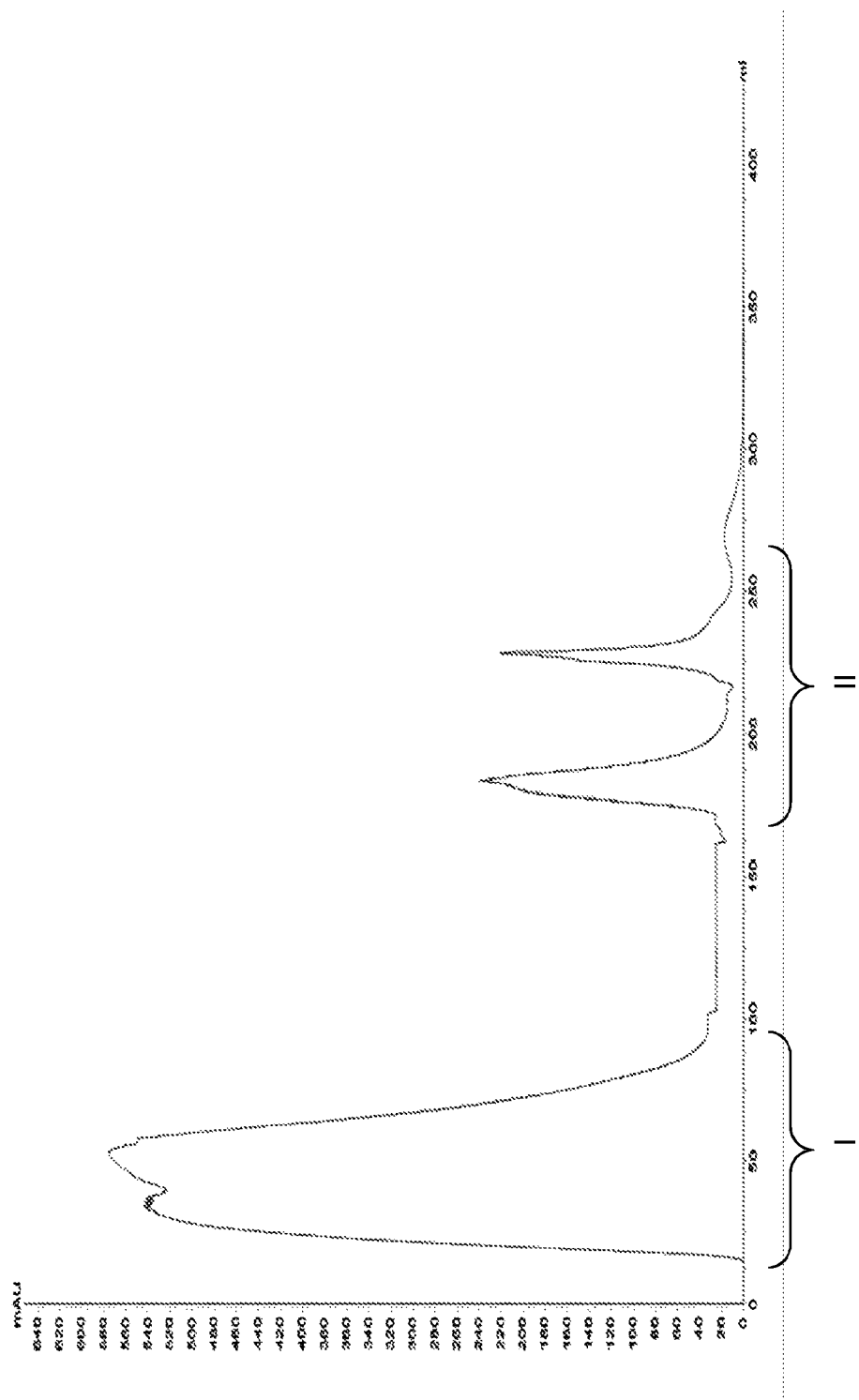

PURIFICATION OF POLYSACCHARIDE PROTEIN CONJUGATES

FILED OF THE INVENTION

The present invention relates to the field of purification of polysaccharide protein conjugates for use as vaccines.

BACKGROUND

Bacterial infections continue to be one of the major cause of diseases inflicting infants and children, particularly in developing countries (Osrin, David et al. (2004) Current Opinion in Infectious Diseases 17(3): 217-224; Thayer, Durrane, and Zaidi, Anita K. M. (2009) Pediatric Infectious Disease Journal 28(1): S3-S9; Sáez-Llorens, Xavier et al. 2003 Lancet 361(9375): 2139-2148; Thapar, Nikhil et al. 2004 Lancet 363(9409): 641-653). The most common pathogens are Haemophilus influenzae type b, Streptococcus pneumoniae, Neisseria meningitidis (Pollard, Andrew J. et al. (2009) Nature Reviews Immunology 9(3): 213-220), Staphylococcus aureus, Shigella, Salmonella, Vibrio cholerae etc. A large number of children die each year as a result of such infections.

Polysaccharide antigens have been one of the major components of bacterial vaccines used to prevent diseases associated with Haemophilus influenzae, Neisseria meningitidis, Streptococcus pneumoniae (Larry K. Pickering et al. (1985) Infectious Diseases Newsletter 4(11): 84-87), and Salmonella enterica serovar Typhi (Hessel L et al. (1999) Eur J Clin Microbiol & Infect Dis., 18(9): 609-620). However, most of the bacterial polysaccharides are T-cell independent antigens preventing development of memory B-cells leading to poor immune response to such antigens in children below two years and elderly persons. Covalent conjugation of polysaccharide antigens to protein carrier bestows them the ability to generate humoral response, and impart them the capabilities of T-cell dependent antigens. Such conjugates have been proven to be efficient in preventing diseases caused by bacterial pathogens. Polysaccharide conjugate vaccines have been licensed for use in many parts of the world for more than two decades (Adams, William G. et al. (1993) JAMA 269(2): 221-226).

Purification of polysaccharide protein conjugates has always been a challenge. Such conjugates are known to be associated with contaminants such as un-reacted polysaccharide (free polysaccharide), un-reacted carrier protein (free protein), low molecular weight conjugates, and other chemicals used for affecting conjugation such as linkers, coupling agents etc. Such contaminants are highly undesirable in a product which is intended for use as a vaccine. For example, a high amount of free polysaccharide is undesirable in a vaccine composition as it might interfere with the immunological function of the conjugate (Peeters, C. A. M. et al. (1992) Vaccine 10(12): 833-840). The contaminants often differ in molecular size, ionic charges and hydrophobicity making it difficult to employ single chromatography step to achieve the purity levels desired for it to be used as vaccine.

Polysaccharide protein conjugates have often been purified from impurities or contaminants by various standard techniques such as density gradient centrifugation, ultrafiltration with ammonium sulfate fractionation (U.S. Pat. No. 6,146,902), ethanol precipitation, gel filtration or size exclusion chromatography, hydrophobic interaction chromatography or ion exchange chromatography.

Ion exchange chromatography has been mostly found suitable to purify the polysaccharides, but it has not been found appropriate to purify conjugates and more particularly when the conjugates are to be purified on a larger scale. Simon, Raphael (WO2012061400) describes a process for polysaccharide protein conjugate purification by binding the conjugate to ion exchange matrix and eluting it subsequently to obtain the purified conjugate. Such processes also results in binding of the free polysaccharide as the conjugate often exhibit charges similar to the free polysaccharide making the purification of conjugate difficult.

Polysaccharide protein conjugates may also be purified using an adsorption method based on hydrophobicity, which will adsorb the conjugate but not the free polysaccharide as the latter tends to be less hydrophobic, by using a high concentration of salt (Lees, Andrew et al. WO2011017101; Pawlowski, Andrzeg (2000) Vaccine 18: 1873-1885). Such purification is achieved by exploiting the hydrophobic nature of the protein which is mainly governed by the proportion of the non-polar surface areas of the protein as well as their spatial distribution. If the conjugated protein is less hydrophobic, hydrophobic interaction chromatography may not be a preferred choice of purifying such conjugates.

Gel filtration chromatography has been most commonly used to purify polysaccharide protein conjugates (Lees, Andrew et al. (1996) Vaccine 14(3): 190-198; Libon, Christine (2002) Vaccine 20: 2174-2180; Jennings, H. J. and Lugòwski, C. (1981) J. Immunology 127: 1011-1018). However such techniques suffer from several limitations. For example, purification using molecular sieving by gel filtration chromatography could only be achieved by sacrificing yields due to inadequate resolution of crude conjugate. Because of the narrow fractionation range, pooling of appropriate fraction containing the desired conjugate requires considerable skills. Any error in collecting fraction could lead to significant loss of the conjugate or increases the risk of association of contaminants with the conjugate as the conjugate and contaminants separate at a very narrow range (see FIG. 1a). Further, it requires large amount of gel filtration matrix, and significantly increased process time, in addition to the difficulties associated with column packing. All these factors lead to higher cost of production which makes the vaccines unaffordable, limiting their wider use in vaccination programs.

The complexity associated with conjugation process usually results in highly heterogeneous array of contaminants often differing in physical and chemical properties such as molecular size, ionic charges, hydrophobicity etc. These factors have made the separation based on single principle of chromatography inadequate to achieve the required degree of purification for the conjugate to be used as vaccine. Therefore, sometimes more than one chromatography steps have been used to purify polysaccharide protein conjugates. Fattom, Ali et al. (Infection and Immunity (1988) 56(9): 2292-2298) describes a two step process of purifying a polysaccharide protein conjugate wherein the conjugate is partially purified over a gel filtration matrix followed by capturing onto a hydrophobic medium to obtain the purified conjugate.

Such methods compromises overall yield of the conjugate due to multiple chromatography steps and also results in increased process time.

Thus production of significant quantities of polysaccharide protein conjugates for use in vaccines has been hindered due to complexities in the prior art processes leading to low yields and high cost of production. Therefore, there is a need to develop alternate method of purification of polysaccharide protein conjugates which offers ease of manufacture, which is less time consuming, and at the same time offering good yields. The present invention provides an unexpectedly efficient method of removing impurities or contaminants from polysaccharide protein conjugates, employing mixed mode chromatography (Orlovsky, Vlad et al (2011) Chromatography Today, 4(3) 24-28; WO2005082483; WO2009131526, WO2010005364). This surprisingly effective method addresses the long-standing problems associated with the prior art processes used to purify polysaccharide protein conjugates. The process of the invention is operationally simple, easily scalable, requires fewer resources, and offers greater yields and product of consistent quality.

SUMMARY OF THE INVENTION

Accordingly, the invention is directed to a method of purification of polysaccharide protein conjugates using mixed mode chromatography which is surprisingly fast and efficient at removing impurities or contaminants. The inventors have found that purifying polysaccharide protein conjugates by mixed mode chromatography simplifies and shortens the process time, effectively removes the contaminants and is easily scalable.

In one of the embodiments, crude polysaccharide protein conjugate is purified from one or more contaminants by contacting the polysaccharide protein conjugate with a mixed mode resin, and collecting unbound purified polysaccharide protein conjugate in the flowthrough.

In one of the embodiments the mixed mode resin comprises of an inert shell and an activated core, preferably an inert porous shell and an activated core with immobilized ligands carrying different functional groups.

In one of the embodiments the conjugate is purified in a single chromatography step by affecting the purification of the conjugate on the basis of size and capturing one or more contaminants by charged interactions and/or hydrophobic interactions.

In one of the embodiments of the single chromatography step, some of the impurities are bound to an ion exchanger, more particularly a positively charged ion exchanger (anion exchanger) while some impurities are bound by hydrophobic interactions.

In one of the embodiments the free polysaccharide is captured by ionic interaction and the free protein is captured by ionic or hydrophobic interaction while the conjugate is collected in a non-binding mode.

In one of the embodiments one or more contaminants are captured under conditions that facilitate binding of said contaminants, preferably under conditions of low conductivity.

In one of the embodiments, the method involves contacting a crude polysaccharide protein conjugate with a mixed mode resin comprising an inert porous shell and an activated core under conditions of low conductivity that allow binding of the contaminants and collecting the unbound polysaccharide protein conjugate in a flowthrough.

In one of the embodiments the polysaccharide protein conjugate purified by the method of the invention is Hib conjugate, meningococcal conjugate, pneumococcal conjugate or typhoid conjugate.

BRIEF DESCRIPTION OF THE DRAWINGS

FIG. 1b—Mixed mode chromatography profile of Hib conjugate representing desired conjugate (I) and contaminants (II) purified by the process of example 2a and example 2b.

DETAILED DESCRIPTION OF THE INVENTION

Figure 1A:
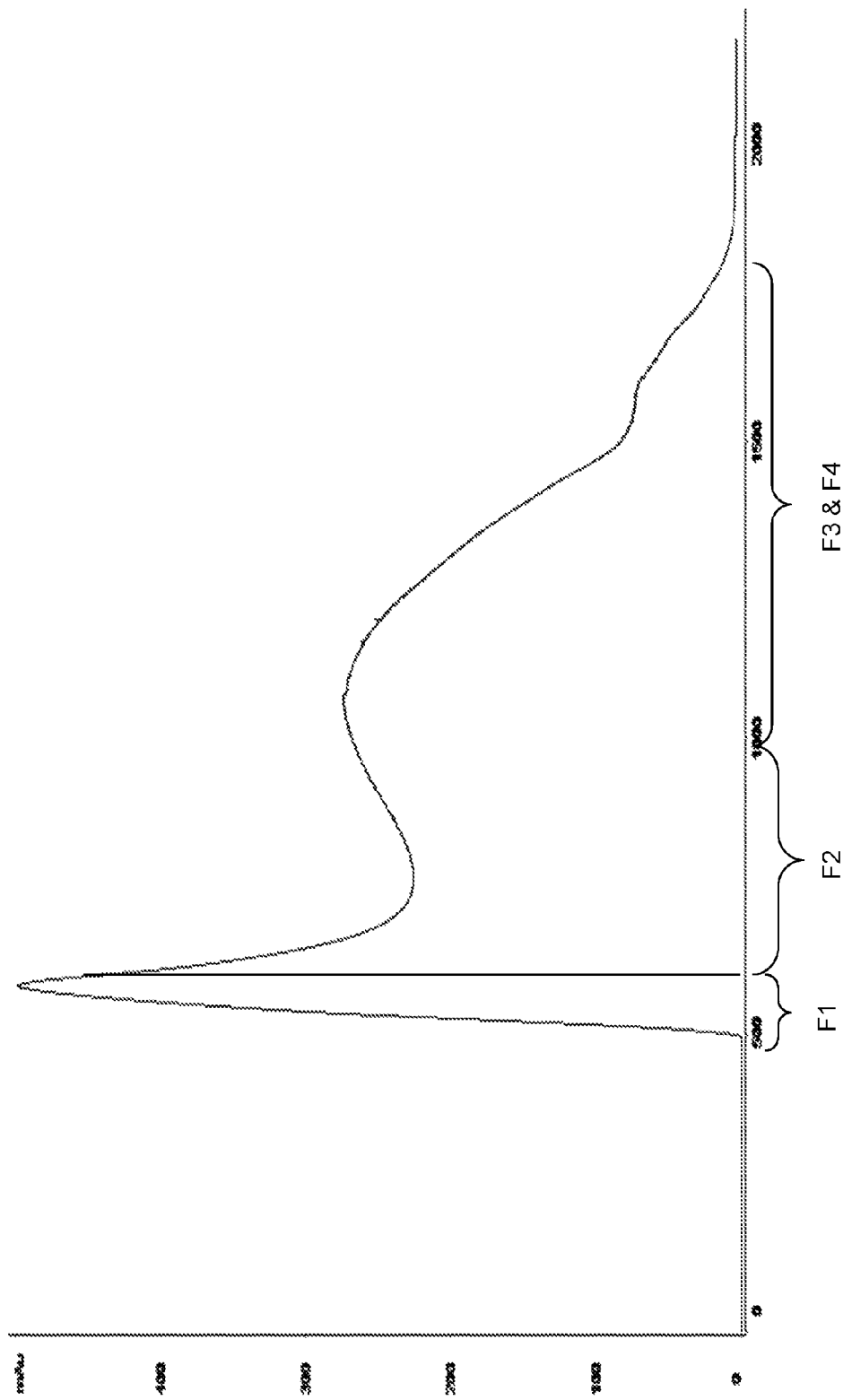
FIG. 1a—Gel filtration chromatography profile of Hib conjugate representing desired conjugate (F-2) and contaminants (F-1, F3 & F4) purified by the process of example 1.

The singular forms "a", "an" and "the" as used in the specification also include plural aspects unless the context dictates otherwise. Similarly, any singular term used in the specification also mean plural or vice versa unless the context dictates otherwise.

It must be noted that the words "comprising" or any of its forms such as "comprise" or "comprises", "having" or any of its forms such as "have" or "has", "including" or any of its forms such as "include" or "includes", or "containing" or any of its forms such as "contain" or "contains" are open-ended and do not exclude additional unrecited elements or method steps.

Wherever any quantity or range is stated one skilled in the art will recognize that quantity or range within 10 or 20 percent of the stated values can also be expected to be appropriate, i.e., where 20% is stated, a range of from 16-18% to 22-24% is implicit and can be appropriate.

The term "buffer" as used herein, includes those agents that maintain the pH of a solution in a desired range. In one of the embodiment pH of the buffer is between about 5.0 to 7.5. In an another embodiment the buffer used is selected from phosphate buffer, Tris buffer, MES buffer, HEPES buffer, citrate buffer or combination thereof, or more preferably a phosphate buffer.

Polysaccharide means a polymer formed by many repeating units joined in either linear or branched manner. The term polysaccharide, as used in the specification, has been interchangeably used to mean saccharide or oligosaccharide. In some embodiments the term polysaccharide means a polymer containing at least about 10 repeat units. A polysaccharide may be depolymerized or sized to contain specified number of repeat units by any process known to the persons skilled in the art, for example acid or alkaline hydrolysis, ozonolysis, periodate oxidation, β-elimination, and enzymatic hydrolysis.

By charged interactions or ionic interactions it is implied that the separation is affected by ion exchangers viz., cation or anion exchangers. An anion exchanger will bind a compound with negative charge while leaving the compounds with positive charge whereas a cation exchanger will bind a compound with positive charge while leaving the compounds with negative charge.

By hydrophobic interactions it is implied that the separation is affected by differences in surface hydrophobicity of the biomolecules. Hydrophobic Interaction Chromatography (HIC) separates biomolecules according to differences in their surface hydrophobicity by utilizing a reversible interaction between the biomolecule and the hydrophobic surface of the HIC medium. The non polar surface areas as well as their spatial arrangement are responsible for differences in the hydrophobicity of the biomolecules.

The terms resin or matrix or medium have been interchangeably used to denote chromatography stationary phase. The term "mixed mode resin" or "mixed mode matrix" or "mixed mode medium" denotes a chromatography resin or matrix or medium to which functional groups, known as ligands, have been immobilized giving the mixed mode resin the ability to interact with target molecules in several different ways. The mixed mode resin may have a porous shell with immobilized ligands inside. In one of the embodiment the mixed mode resin contains an inert porous shell and a ligand activated core. The mixed mode resin may also be referred to as multimodal resin or multimodal matrix or multimodal medium.

In one of the embodiments some of the impurities or contaminants will interact with the hydrophobic functionality of the ligand while some other impurities or contaminants will interact with ionic functionality of the ligand thereby affecting separation of the contaminants from the polysaccharide protein conjugates.

"Non-binding mode" "unbound mode" or "Negative chromatography" means a chromatographic technique where the desired product is purified in a manner where it does not bind to the chromatography matrix i.e., the desired product passes through the void spaces of the chromatography matrix and is collected in the flowthrough or capture pool.

During the process of conjugation of polysaccharide to carrier proteins not all molecules of polysaccharide and protein in the conjugation mixture are coupled to form polysaccharide protein conjugate. As a result the conjugate is associated with contaminants such as free polysaccharide, free protein, polysaccharide derivatized with linker, carrier protein derivatized with linker, coupling agents etc., depending upon the type of conjugation chemistry used to prepare such conjugates. For example, if the conjugate is prepared by direct linking of polysaccharide with carrier protein the conjugate is expected to be associated with free polysaccharide, free carrier protein, residual coupling agents or mixtures thereof. If the conjugate is prepared by derivatizing the polysaccharide or protein with a linker the conjugate is expected to be associated with derivatized polysaccharide or derivatized carrier protein in addition to underivatized polysaccharide or underivatized carrier protein or mixtures thereof.

The term impurities or contaminants have been used interchangeably to refer to any chemical or biological molecule other than polysaccharide protein conjugate intended for use as vaccine. Polysaccharide protein conjugates are normally associated with contaminants such as, but not limited to, free polysaccharide, free protein, low molecular weight conjugates, linkers, coupling agents or mixtures thereof.

Crude conjugate or crude polysaccharide protein conjugate means a polysaccharide protein conjugate which has not been purified or partially purified to render it free from one or more of its associated contaminants or impurities. Such crude conjugate often contain impurities such as, but not limited to, free polysaccharide, free carrier protein, low molecular weight conjugates, higher aggregates, residual amounts of linkers, coupling agents or mixtures thereof. The process of the invention is suitable to purify any polysaccharide protein conjugate from one or more of its associated contaminants.

The term free polysaccharide or derivatized polysaccharide has been used interchangeably to mean a polysaccharide antigen which is not conjugated to carrier protein. Thus the term free polysaccharide comprises of free polysaccharide, polysaccharide derivatized with linker or mixtures thereof.

The term free protein or derivatized protein has been used interchangeably to mean a carrier protein which is not conjugated to polysaccharide antigen. Thus the term free carrier protein comprises of free carrier protein, carrier protein derivatized with linker or mixtures thereof.

Low molecular weight conjugate means a conjugate by virtue of its size has the ability to enter the activated core of the mixed mode matrix through the pores of the inert shell. In one of the embodiment such lower molecular weight conjugates have molecular size less than 2000 kDa, less than 1800 kDa, less than 1600 kDa, less than 1400 kDa, less than 1200 kDa, less than 1000 kDa, less than 900 kDa, less than 800 kDa, less than 700 kDa, less than 600 kDa, less than 500 kDa, less than 400 kDa, less than 300 kDa, less than 200 kDa, less than 100 kDa or mixtures thereof.

"Purified polysaccharide protein conjugate" or "purified conjugate" has been used interchangeably to mean a conjugate which has been rendered free from associated contaminants such that the quantity of that contaminant is reduced by about 50% or more, about 60% or more, about 70% or more, about 80% or more, and about 90% or more. In one of the embodiments, the quantity of the contaminant is reduced by 80% or more, 85% or more, 90% or more, or 95% or more. A "purified conjugate" or "purified polysaccharide protein conjugate" is also understood to mean a conjugate which has been rendered free from associated contaminants, especially with respect to free polysaccharide and free protein content, to a degree specified by pharmacopoeial specification, or regulatory authority or established by relevant immunological correlate for the conjugate. For example in case of Hib polysaccharide conjugated to tetanus toxoid the free polysaccharide contents should be less than 20% and free tetanus toxoid should be less than 1% and at least 60% of the conjugate should have molecular size distribution within 0.2 $K_D$ (distribution coefficient) when assessed by size exclusion chromatography on sepharose CL-4B (*Haemophilus* Type b Conjugate Vaccine, Indian Pharmacopoeia, 2010 Vol 3 pg 2395-2398). The techniques to measure molecular size distribution are well known to the person skilled in the art (WHO Technical Report Series, No. 897, 2000 pg 27-56; WHO Technical Report Series No. 658, 1981, Annex 6; McCauley, J. A. et al. J Biol Stand (1981) 9: 461-468; Parisi, L et al. (1999) J Chromatogr A 847: 209-211). Similarly free polysaccharide and free protein content can be measured by any quantitative techniques known to person skilled in the art (Tsai, C. M. et al. (1994) Vaccine 12(8): 700-706; Ashwell, G. Methods Enzymology, (1957) 3: 73-105; Guo, Y Y et al. (1998) Biologicals 26(1):33-38; Lei, Q P et al. (2000) Dev Biol (Basel) 103: 259-264; Stoscheck, Christa M. (1990) Methods in Enzymology 182: 50-68). In a polysaccharide protein conjugate vaccine it is advisable to keep the level of contaminants as low as possible, especially with respect to free polysaccharide, as the conjugate may undergo degradation during the shelf life thereby leading to an increase in the free polysaccharide content in the vaccine which can have adverse impact on the immunogenicity of the polysaccharide protein conjugate. In one of the embodiments, the free polysaccharide content is 15% or less, 14% or less, 13% or less, 12% or less, 11% or less, 10% or less, 9% or less, 8% or less, 7% or less, 6% or less, 5% or less, 4% or less, 3% or less, or 2% or less. In one of the embodiments, the free polysaccharide content is between 10-15%, between 5-10%, or between 0-5%.

The polysaccharide antigens that can be used to produce the conjugate may be obtained from various bacteria that are known to those skilled in the art. Exemplary bacteria include—*Haemophilus influenzae* type b (for example, *H. influenza* capsular polysaccharide—polyribosyl ribitol phosphate [PRP]), *Neisseria meningitidis* (for example *N. meningitidis* serogroup A capsular polysaccharide (MenA), *N. meningitidis* serogroup C capsular polysaccharide (MenC),

*N. meningitidis* serogroup Y capsular polysaccharide (MenY), *N. meningitidis* serogroup W capsular polysaccharide (MenW)), *Streptococcus pneumoniae* (such as serotypes 1, 2, 3, 4, 5, 6B, 7F, 8, 9N, 9V, 10A, 11A, 12F, 14, 15B, 17F, 18C, 19A, 19F, 20, 22F, 23F and 33F), *Staphylococcus aureus, Salmonella enterica serovar Typhi, Vibrio cholerae, Shigella flexneri* etc. The polysaccharide antigens of particular interest are those that are obtained from the capsular polysaccharide of *Haemophilus influenzae* type b, *Neisseria meningitidis, Streptococcus pneumoniae* and *Salmonella enterica serovar Typhi*.

The carrier proteins that may be used to conjugate the polysaccharide are known to those skilled in the art. The commonly used carrier protein for making the conjugates are diphtheria toxoid or a non-toxic mutant such as $CRM_{197}$, tetanus toxoid, pertussis toxoid, outer membrane protein C of *Neisseria meningitidis*, protein-D of *Haemophilus influenzae*, outer membrane protein C of *Salmonella*, pneumolysin (including detoxified variants), pneumococcal surface protein A (PspA), or pneumococcal adhesin protein (PsaA) of *Streptococcus pneumoniae*, recombinant *Pseudomonas aeruginosa* exotoxin A (rEPA) etc.

The polysaccharide protein conjugate vaccines may be prepared by covalently attaching purified bacterial capsular polysaccharides to protein molecules using a variety of chemical methods. For example, the conjugate may be prepared as described by Schneerson, R. et al. (1980) J. Exp. Med. 152: 361-476; Chu, chiayung et al. (1983) Infection and Immunity 40(1): 245-256. The polysaccharide is first activated in the presence of cyanogen bromide to generate a cyanate ester. The activated polysaccharide is then linked (derivatized) to the spacer, for example, adipic dihydrazide. It is also possible to directly link spacer without activation of the polysaccharide. The derivatized polysaccharide (PS-AH) is conjugated to the carrier protein using carbodiimides such as 1-ethyl-3-(3-dimethylaminopropyl (EDAC or EDC), N,N-Dicyclohexyl carbodiimide (DCC), or N,N-Diisopropyl carbodiimide (DIC). It is also possible to first derivatize the protein, and such derivatized protein may then be conjugated to the polysaccharide as described by Laferriere, Craig (2011) Glycoconjugate Journal 28: 463-472; Silveira, I. A. et al (2007) Vaccine 25: 7261-7270; U.S. Pat. No. 4,496,538.

Activation of polysaccharide may also be achieved by organic cyanylating agents such as 1-cyano-4-dimethyl-amino pyridinium tetrafluoroborate (CDAP), N-cyanotriethylammonium tetrafluoroborate (CTEA), and p_Nitrophenylcyanate (pNPC) as described by Lees, Andrew U.S. Pat. No. 5,693,326; Lees, Andrew et al. (1996) Vaccine 14(3): 190-198.

Alternatively, polysaccharides, or fragments thereof, may be activated selectively at their terminal reducing ends by introducing aldehydes which may be directly or indirectly (through a linker or spacer) coupled to carrier protein by reductive amination (Jennings, H. J. U.S. Pat. No. 4,356,170; P. W. Anderson, et al. (1986) J. Immunol. 137: 1181-1186; Gray G R. (1978) Methods Enzymology; 50: 155-160).

The polysaccharide protein conjugate that are contemplated to be purified by the process of the invention are preferably Hib conjugate, meningococcal conjugates, pneumococcal conjugates, and typhoid conjugate.

*Haemophilus influenzae* polysaccharide protein conjugate (Hib conjugate) may be prepared by conjugating the capsular polysaccharide (PRP) obtained from *Haemophilus influenzae* type b (Hib) to carrier protein. PRP is a polymer of ribose ribitol phosphate which may be coupled to carrier protein such as, but not limited to, tetanus toxoid, diphtheria toxoid or a non-toxic mutant thereof, protein D of *Haemophilus influenzae*, outer membrane protein C of *Neisseria meningitidis*, outer membrane protein C of *Salmonella*, pneumolysin (including detoxified variants), PspA, PsaA, or rEPA. Methods of preparing Hib conjugate are well known to those skilled in the art (Chu, chiayung et al. (1983) Infection and Immunity 40(1): 245-256; U.S. Pat. Nos. 4,496,538; 4,459,286; and 4,619,828).

Meningococcal conjugates may be prepared from the capsular polysaccharide of *Neisseria meningitidis* (for example *N. meningitidis* serogroup A capsular polysaccharide (MenA), *N. meningitidis* serogroup C capsular polysaccharide (MenC), *N. meningitidis* serogroup Y capsular polysaccharide (MenY), *N. meningitidis* serogroup W capsular polysaccharide (MenW)), by coupling the capsular polysaccharide to carrier protein such as, but not limited to, tetanus toxoid, diphtheria toxoid or its non-toxic mutant thereof, protein D of *Haemophilus influenzae*, outer membrane protein C of *Neisseria meningitidis*, outer membrane protein C of *Salmonella*, pneumolysin (including detoxified variants), PspA, PsaA or rEPA. Methods of preparing meningococcal conjugates are well known to those skilled in the art (Silveira, L A. et al (2007) Vaccine 25: 7261-7270; U.S. Pat. No. 4,356,170; WO2007000343).

Pneumococcal conjugates may be prepared from the capsular polysaccharides of *Streptococcus pneumoniae* serotpyes (for example, serotypes such as 1, 2, 3, 4, 5, 6B, 7F, 8, 9N, 9V, 10A, 11A, 12F, 14, 15B, 17F, 18C, 19A, 19F, 20, 22F, 23F and 33F) by coupling the capsular polysaccharide to carrier protein such as, but not limited to, tetanus toxoid, diphtheria toxoid or its non-toxic mutant thereof, protein D of *Haemophilus influenzae*, outer membrane protein C of *Neisseria meningitidis*, outer membrane protein C of *Salmonella*, pneumolysin (including detoxified variants), PspA, PsaA or rEPA. Methods of preparing pneumococcal conjugates are well known to those skilled in the art (Laferriere, Craig et al. (1997) Vaccine 15(2): 179-186; U.S. Pat. No. 4,673,574; WO2007000343).

Typhoid conjugate may be prepared by conjugating the capsular polysaccharide (vi antigen—a homopolymer of $\alpha$-(1→4)-D-galactosaminuronic acid, N-acetylated at C-2 and O-acetylated at C-3) obtained from *Salmonella enterica serovar Typhi* to carrier protein such as, but not limited to, tetanus toxoid, diphtheria toxoid or its non-toxic mutant thereof, protein D of *Haemophilus influenzae*, outer membrane protein C of *Neisseria meningitidis*, outer membrane protein C of *Salmonella*, pneumolysin (including detoxified variants), PspA, PsaA or rEPA. Method of preparing typhoid conjugate is well known to those skilled in the art (Kossaczka et al. (1999) Infection & Immunity 67(11) 5806-5810; Micoli F. et al. (2011) Vaccine 29(4): 712-720).

The present invention is neither limited to any of the approaches that may be used to conjugate polysaccharide to carrier protein nor to the type of polysaccharide or the carrier protein to make polysaccharide protein conjugates. For example, Jennings, Harold J. et al. (Bacterial polysaccharide vaccines: Glycoconjugates and peptide-mimetics in Microbial Glycobiology Structures, Relevance and Applications Academic Press, 2010, Pages 933-956) gives a general outline of various approaches that may be used to prepare the polysaccharide protein conjugate. Conjugates prepared by any method known to the person skilled in the art can be purified by the method of the invention.

Purification of Conjugate Using Mixed Mode Chromatography

The invention uses mixed mode chromatography medium for the purification of polysaccharide protein conjugate from the contaminants. In a mixed mode chromatography, two or more different chromatography principles are employed to achieve separation of desired molecule from its associated impurities in a single step.

The crude conjugate is loaded onto the mixed mode chromatography matrix. Optionally the loading mixture may be membrane filtered, preferably by diafiltration, before being loaded onto the mixed mode chromatography matrix. Diafiltration may be performed either in batch (discontinuous) or continuous processing mode using a membrane having a wide range of molecular weight cut off such as between 30 kDa to 1000 kDa. In one of the embodiments, the membrane has a molecular weight cut off between 30 kDa to 900 kDa, between 30 kDa to 800 kDa, between 30 kDa to 700 kDa, between 30 kDa to 600 kDa, between 30 kDa to 500 kDa, between 30 kDa to 400 kDa, between 30 kDa to 300 kDa, between 30 kDa to 200 kDa, between 30 kDa to 200 kDa, or between 30 kDa to 100 kDa. A mixed mode chromatography matrix is the one having an inert shell and an activated core. The inert shell is provided with pores which allow molecules under a certain size to enter the activated core imparting size exclusion property to the matrix while the activated core is immobilized with ligands having different functional groups. A typical mixed mode matrix has an inert porous shell and a ligand activated core.

The porosity of the matrix determines the size of the molecule that may be excluded from entering the ligand activated core. In one of the embodiments the pore size of the inert porous shell has a molecular size cut-off of about 100 kDa, about 200 kDa, about 300 kDa, about 400 kDa, about 500 kDa, about 600 kDa, about 700 kDa, about 800 kDa, about 900 kDa, about 1000 kDa, about 1200 kDa, about 1400 kDa, about 1600 kDa, about 1800 kDa, or about 2000 kDa which will exclude the entry of molecules having size greater than the molecular size cut-off from entering the ligand activated core. In one of the embodiments, the pore size of the inert porous shell has a molecular size cut-off of about 200 kDa to about 2000 kDa, about 500 kDa to about 1500 kDa, about 600 kDa to about 1000 kDa. In one of the preferred embodiments the inert porous shell has a molecular size cut-off of about 700 kDa preventing the entry of molecules having size greater than 700 kDa from entering the ligand activated core.

Thus, by using a matrix of desired porosity, it is now possible to separate the polysaccharide protein conjugates from its contaminants such that the latter enter the core and are captured by the functional groups of the ligands while the purified polysaccharide protein conjugate is recovered in a flowthrough in an unbound mode.

The ligands may be the ones having different functional groups, which have the ability to interact with target molecules in several different ways, such as octylamine, N-Benzyl-N-methyl ethanolamine, mercapto-benzimidazole-sulphonic acid. For example an octylamine ligand can interact with target molecules by both hydrophobic and ionic interactions because of the presence of alkyl chain (8 carbon octyl chain) and amino group. Similarly, in N-Benzyl-N-methyl ethanolamine an ionic quaternary ammonium group is complemented by hydrophobic phenyl group offering dual functionality. In mercapto-benzimidazole-sulphonic acid the aromatic ring imparts hydrophobic interactivity while $SO_3^-$ substituent imparts ionic interaction capability. Matrices with such functionalities are available from various manufacturers such as GE HealthCare, Pall Life Sciences, etc. It is also possible to have more than one type of ligand in the core each participating in single interaction (viz., hydrophobic or ionic) rather than only one type of ligand offering dual functionality. In one of the embodiments the ligand activated core is functionalized with octylamine ligands.

In one of the embodiments the process involves capturing the contaminants by hydrophobic and/or ionic interactions and recovering or collecting the conjugate in a non-binding mode.

In one of the embodiments the contaminants or impurities enter the ligand activated core through the pores of the inert porous shell and interact with the hydrophobic and/or ionic functionality of the ligands, while the conjugate is recovered in a non-binding mode.

In one of the embodiments the mixed mode chromatography medium preferably used to purify polysaccharide protein conjugate has an inert porous shell with a molecular size cutoff of 700 kDa and an activated core comprising octylamine ligands (for example Capto™ Core 700, GE Health Care).

In one of the embodiments the polysaccharide protein conjugate to be purified is selected from Hib conjugate, meningococcal conjugate, pneumococcal conjugate or typhoid conjugate, or more preferably Hib conjugate.

The column before loading is pre equilibrated with a buffer. Any suitable buffer known in the art, but not limited to, phosphate, Tris, MES, HEPES, citrate, or their combination may be used. It is preferable to use such buffering agents which are suitable for maintaining a pH range of at least about pH 5.0-7.5.

In one of the embodiment the pH of the buffer is between 5.0 to 7.5, between 5.0 to 7.0, between 5.1 to 6.9 between 5.2 to 6.8 between 5.3 to 6.7, between 5.4 to 6.6, between 5.5 to 6.5, between 5.6 to 6.4, between 5.7 to 6.3, between 5.8 to 6.2, between 5.9 to 6.0 or pH 6.0. The pH may be maintained by addition of acid/base as required.

The buffers that may be used during the method of the invention has conductivity below 20 mS/cm, below 15 mS/cm, below 10 mS/cm, below 9 mS/cm, below 8 mS/cm, below 7 mS/cm, below 6 mS/cm, below 5 mS/cm, below 4 mS/cm, below 3 mS/cm, below 2 mS/cm, below 1 mS/cm, below 0.9 mS/cm, below—0.8 mS/cm, below 0.7 mS/cm, below 0.6 mS/cm, below 0.5 mS/cm, below 0.4 mS/cm, below 0.3 mS/cm, below 0.2 mS/cm, or below 0.1 mS/cm. Conductivity as used herein refers to the ability of a solution, such as a buffer solution, to influence electrostatic interactions, for example binding to or release of, of the contaminants with the matrix. The conductivity may be adjusted by varying ionic concentration of the buffer composition. Generally low conductivity buffers are preferable. By low conductivity it is understood that the conductivity is below 10 mS/cm, preferably below 5 mS/cm, and most preferably below 3 mS/cm. In one of the embodiments, the conductivity of the buffer is between about 8 mS/cm to about 0.5 mS/cm, between about 5 mS/cm to about 1 mS/cm, between about 4 mS/cm to about 1.5 mS/cm, between about 3 mS/cm to about 2 mS/cm.

In one of the embodiments, an exemplary buffer contains 10 mM phosphate, pH 5.8 to 6.2 with a conductivity of approximately 2 mS/cm.

The conjugate is loaded at the rate of 2-120 cm/hr. Preferably at the rate of 10-120 cm/h, 20-110 cm/h, 30-100 cm/h, 40-90 cm/h, 50-80 cm/h, or 60-70 cm/h. The flow rate can be adjusted so as to allow sufficient time for the contaminants to interact with the matrix. Sample may be loaded at 300 cm/hr or higher with one or more repeated steps of loading. If required, the crude conjugate may be membrane filtered before loading onto the chromatography column. The desired conjugate passes through the void spaces of the mixed mode resin and is collected in the flowthrough while the impurities are trapped inside the ligand activated core by hydrophobic and/or ionic interactions. A wash is given to the column using the phosphate buffer, pH 5.8 to 6.2 to collect the remaining conjugate non-specifically adhering to the matrix. The purified conjugate is diluted with a high conductivity dilution buffer, pH 5.8 to 6.2, and filtered through a 0.45µ and 0.22µ filters.

TABLE 1

Free polysaccharide (PRP), Free carrier protein (TT) and EDC content after purification of polysaccharide protein conjugate (Hib Conjugate) by mixed mode chromatography.

| a | b | c | d | e |
|---|---|---|---|---|
| Batch 111 | | | | |
| Free PRP | 6.0 mg/mL | 0.104 mg/mL | 1.7 | 98.3 |
| Free TT | 2.0 mg/mL | 0.013 mg/mL | 0.7 | 99.3 |
| EDC | 1228 ng/µg of PRP | 0.209 ng/µg of PRP | 0.1 | 99.9 |
| Batch 112 | | | | |
| Free PRP | 6.0 mg/mL | 0.068 mg/mL | 1.1 | 98.9 |
| Free TT | 2.0 mg/mL | 0.010 mg/mL | 0.5 | 99.5 |
| EDC | 1228 ng/µg of PRP | 0.136 ng/µg of PRP | 0.1 | 99.9 |

Column (a) represents the contaminants.
Column (b) represents the amount of contaminants before purification of polysaccharide protein conjugate by mixed mode chromatography.
Column (c) represents the residual amount of contaminants after purification of polysaccharide protein conjugate by mixed mode chromatography.
Column (d) represents the percentage of residual amount of contaminants.
Column (e) represents the percentage reduction of contaminants.

Free PRP was determined by the method described by Tsai, C. M. et al. (1994) Vaccine 12(8): 700-706.

Free protein in a polysaccharide conjugate vaccine may be determined by the methods known to the persons skilled in the art. The amount of free Tetanus toxoid (free TT) in Hib conjugate (PRP conjugated to tetanus toxoid) was determined by strong anion exchange chromatography using a fluorescence detector. The molecules with weak ionic interactions are eluted first (free TT) followed by molecules with strong ionic interactions (Hib conjugate). The free TT was eluted by lowering the pH of the mobile phase below the pI of the tetanus toxoid. The amount of free TT was quantified by comparing the peak area of the sample with the peak area of the standard curve plotted against the concentration (µg/mL) generated using tetanus toxoid.

Capillary Zone Electrophoresis (CZE) was used to quantify 1-ethyl-3-(3-dimethylaminopropyl) carbodiimide (EDC) by directly detecting in capillaries by UV absorbance at 200 nm EDC content in the sample was quantified by comparing peak areas of the sample with the peak areas of the standard curve generated using different concentrations of EDC.

TABLE 2

Molecular size distribution of Hib conjugate purified by mixed mode chromatography

| Sample | Fractionation Range in $K_D$ | Total PRP content (A + B + C) in µg | PRP (µg) | Molecular Size distribution (%) |
|---|---|---|---|---|
| A | <0.2 | 943.1 | 749.06 | 79.4 |
| B | 0.2-0.5 | | 104.83 | 11.1 |
| C | 0.5-1.0 | | 89.21 | 9.5 |

Figure 2:
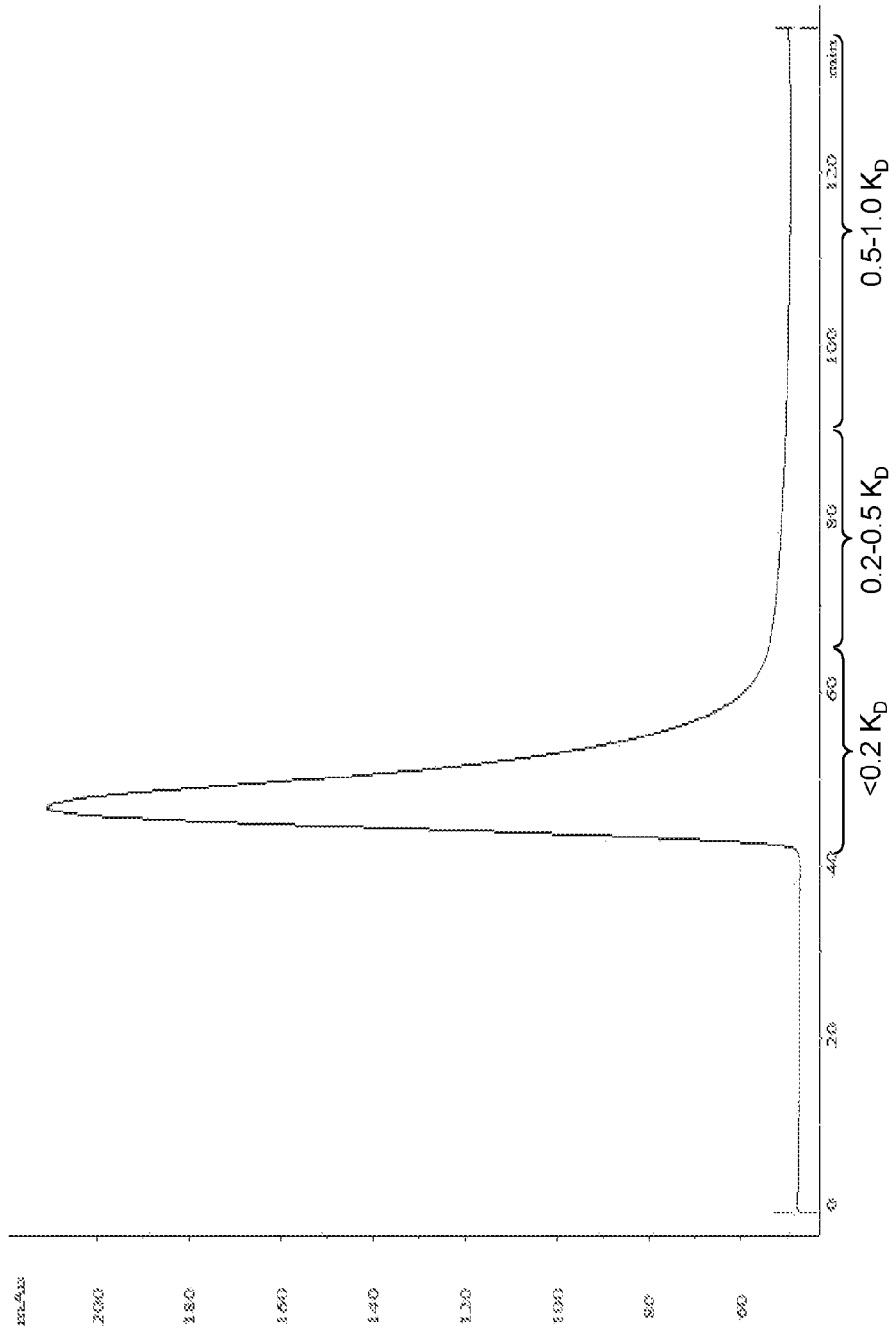
FIG. 2—Molecular size distribution of Hib conjugate purified by mixed mode chromatography.

Molecular size distribution of purified Hib conjugate was analyzed by Sepharose CL4B chromatography (WHO Technical Report Series, No. 897, 2000 pg 27-56) Three fractions of Size distribution ranges i.e., <0.2, 0.2-0.5 and 0.5-1.0 $K_D$ as shown in FIG. 2 were collected and PRP content was analyzed. The results indicate that 79.4% of conjugate is in the molecular size range of <0.2 $K_D$ indicating that mixed mode chromatography efficiently removes low molecular weight conjugate.

The present invention is further exemplified by the following non limiting examples. It should be understood that the examples are provided to illustrate the invention. From the description and the exemplified embodiments and examples, on skilled in the art can make various modifications or adaptations to the invention. Such modifications or adaptations are deemed to be within the scope and the spirit of the invention.

EXAMPLES

Example 1

Purification of Hib Conjugate Using Gel Filtration Chromatography (3.0 L Scale)

The chromatography column (BPG, GE Healthcare) packed with Sepharose CL-2B (GE Healthcare) is equilibrated with equilibration buffer (10 mM Phosphate buffer containing 0.2 M NaCl). 3000 mL of crude Hib conjugate (Hib polysaccharide conjugated to tetanus toxoid) is loaded onto the pre equilibrated column. The crude conjugate gets fractionated (Fraction-1 to Fraction-4) based upon distribution coefficient (Kd), from which the desired conjugate (Fraction-2) is collected in a flowthrough. Rest of the fractions (Fraction-1, Fraction-2 and Fraction-3) contains contaminants (FIG. 1a).

Example 2a

Purification of Hib Conjugate Using Mixed Mode Chromatography (0.08 L Scale)

80 mL of crude Hib conjugate i.e., Hib polysaccharide conjugated to tetanus toxoid (concentration 10 mg/mL, pH 5.8 and conductivity 20 mS/cm) is diluted 10 times with equilibration buffer (10 mM Sodium phosphate, pH 5.8 and conductivity 2 mS/cm) and concentrated to approximately five times its volume using 1000 kDa cassette (Millipore Biomax). The conjugate is continuously diafiltered (using 30 kDa membrane) with equilibration buffer for about 20 times and concentrated to its initial volume.

The mixed mode matrix (Capto™ Core 700 matrix, GE Healthcare) packed in BPG column (GE Healthcare) is equilibrated with equilibration buffer and the conjugate is loaded at the rate of 10 cm/h. The unbound conjugate is collected. A wash is given to the column using the equilibration buffer to collect the remaining conjugate non-specifically adhering to the matrix. The conjugate collected is diluted using phosphate buffer pH 5.8-6.2 and filtered through 0.45µ and 0.2µ filter.

Example 2b

Purification of Hib Conjugate Using Mixed Mode Chromatography (3.0 L Scale)

3000 mL of crude Hib conjugate i.e., Hib polysaccharide conjugated to tetanus toxoid (concentration 10 mg/mL, pH 5.8 and conductivity 20 mS/cm) is diluted 10 times with equilibration buffer (10 mM Sodium phosphate, pH 5.8 and conductivity 2 mS/cm) and concentrated to approximately 3 times its volume using 1000 kDa cassette (Millipore Biomax). The conjugate is continuously diafiltered (using 30 kDa membrane) with equilibration buffer for about 25 times and concentrated to its initial volume.

The mixed mode matrix (Capto™ Core 700 matrix, GE Healthcare) packed in Axichrom column (GE Healthcare) is equilibrated with equilibration buffer and the conjugate is loaded at the rate of 60 cm/h. The unbound conjugate is collected. A wash is given to the column using the equilibration buffer to collect the remaining conjugate non-specifically adhering to the matrix. The conjugate is diluted using phosphate buffer pH 5.8-6.2 and filtered through 0.45µ and 0.2µ filter.

TABLE 3

Advantages of using mixed mode chromatography over gel filtration chromatography for conjugate purification

| S. No. | Parameters | Gel filtration chromatography | Mixed mode chromatography |
|---|---|---|---|
| 1 | Batch size | 3.0 L | 3.0 L |
| 2 | Matrix volume used | 60.0 L | 3.0 L |
| 3 | Column height | 90 cm | 18 cm |
| 4 | Column diameter | 300 mm | 140 mm |
| 5 | buffer requirement | 1000 L | 200 L |
| 6 | Pooling criteria | Specified region of inner fraction (contaminants and conjugate separate over a very narrow range increasing the risk of contamination, see FIG. 1a.) | Unbound fraction (contaminants and conjugate separate over a broad range reducing the risk of contamination, see FIG. 1b.) |
| 7 | Column packing, unpacking and chromatographic run operations | Cumbersome, inconvenient and highly time consuming operations | Very simple, convenient and easy |
| 8 | Overall process time | 6 days | <1 day |
| 9 | Nature of chromatography | Fractionation by size exclusion | Negative chromatography/non-binding mode |
| 10 | Principle involved | Size Exclusion | Size exclusion, ion exchange & Hydrophobic |

The invention claimed is:

1. A process of purifying a polysaccharide protein conjugate from one or more contaminants comprising the steps of:
   a. contacting a crude polysaccharide protein conjugate with a mixed mode resin comprising an inert porous shell and an activated core under conditions of low conductivity that allow binding of said contaminants, and
   b. collecting the unbound polysaccharide protein conjugate in a flowthrough,
   wherein a size of the unbound polysaccharide protein conjugate is greater than a molecular size cut-off of a pore size of the inert porous shell,
   wherein the polysaccharide protein conjugate is selected from the group consisting of Hib conjugate, meningococcal conjugate, pneumococcal conjugate and typhoid conjugate,
   wherein the inert porous shell comprises pores having a molecular weight cut off between 2000 kDa to 500 kDa, and
   wherein the method further comprises a dilution step and a diafiltration step before step (a).

2. The process as claimed in claim 1, wherein the molecular weight cut off is between 1000 kDa to 700 kDa.

3. The process as claimed in claim 2, wherein the activated core is immobilized with ligands comprising functional groups.

4. The process as claimed in claim 3, wherein the functional groups on the immobilized ligand comprises of an alkyl chain and an amino group.

5. The process as claimed in claim 4, wherein the alkyl chain comprises 4-14 carbons.

6. The process as claimed in claim 5, wherein the alkyl chain interacts with the contaminants by hydrophobic interactions.

7. The process as claimed in claim 6, wherein the amino group interacts with the contaminants by ionic interactions.

8. The process as claimed in claim 7, wherein the contaminants comprises of free polysaccharide.

9. The process as claimed in claim 6, wherein the contaminants comprises of free protein.

10. The process as claimed in claim 6, wherein the contaminants comprises of low molecular weight conjugates.

11. The process as claimed in claim 6, wherein the contaminants comprises of linkers or coupling agents.

12. The process as claimed in claim 1, wherein step (a) is performed by loading the polysaccharide protein conjugate onto a chromatography column comprising the mixed mode resin comprising the inert porous shell and the activated core under conditions of low conductivity that allow binding of said contaminants.

13. The process as claimed in claim 12, wherein the loading is performed at a flow rate of 2-120 cm/h.

14. The process as claimed in claim 13, wherein the flow rate is between 10-120 cm/h.

15. The process as claimed in claim 14, wherein the flow rate is between 10-80 cm/h.

16. The process as claimed in claim 12, wherein the low conductivity means a conductivity below 10 mS/cm.

17. The process as claimed in claim 16, wherein the conductivity is maintained by adjusting ionic concentration of a buffer.

18. The process as claimed in claim 17, wherein the buffer is selected from phosphate, Tris, MES, HEPES, citrate or combination thereof.

19. The process as claimed in claim 18, wherein the buffer has a pH between 5.0 to 7.5.

20. The process as claimed in claim 19, wherein the buffer is a phosphate buffer.

21. The process as claimed in claim 20, wherein the buffer has a conductivity below 5 mS/cm.

22. The process as claimed in claim 1, wherein the diafiltration is performed continuously for 20-25 times.

23. The process as claimed in claim 22, wherein the diafiltration is performed over a membrane with a molecular weight cutoff of 30 kDa.

24. The process according to claim 1, further comprising producing a vaccine comprising the substantially purified polysaccharide protein conjugate.

25. The process as claimed in claim 1, wherein the polysaccharide protein conjugate comprises Hib conjugate.

* * * * *